United States Patent
Odrich et al.

(10) Patent No.: US 6,733,292 B2
(45) Date of Patent: May 11, 2004

(54) UNIVERSAL IMPLANT

(75) Inventors: Ronald B. Odrich, Bronx, NY (US); Alan S. Pollack, Hastings-on-Hudson, NY (US)

(73) Assignee: Park Avenue Periodontal Associates, P.C., New York, NY (US)

( * ) Notice: Subject to any disclaimer, the term of this patent is extended or adjusted under 35 U.S.C. 154(b) by 100 days.

(21) Appl. No.: 10/122,988

(22) Filed: Apr. 15, 2002

(65) Prior Publication Data

US 2003/0194679 A1 Oct. 16, 2003

(51) Int. Cl.$^7$ ................................................ A61C 8/00
(52) U.S. Cl. ....................................................... 433/173
(58) Field of Search ................................. 433/172, 173, 433/174, 175, 176, 141

(56) References Cited

U.S. PATENT DOCUMENTS

| | | | |
|---|---|---|---|
| 4,411,624 A | 10/1983 | Ogino et al. | 433/173 |
| 4,758,160 A | 7/1988 | Ismail | 433/173 |
| 4,863,383 A | 9/1989 | Grafelmann | 433/174 |
| 4,960,381 A | 10/1990 | Niznick | 433/174 |
| 5,199,873 A | 4/1993 | Schulte et al. | 433/174 |
| 5,281,140 A * | 1/1994 | Niznick | 433/172 |
| 5,302,126 A * | 4/1994 | Wimmer et al. | 433/173 |
| 5,417,570 A | 5/1995 | Zuest et al. | 433/177 |
| 5,437,551 A | 8/1995 | Chalifoux | 433/173 |
| 5,636,989 A * | 6/1997 | Somborac et al. | 433/173 |
| 5,651,675 A | 7/1997 | Singer | 433/172 |
| 5,667,384 A * | 9/1997 | Sutter et al. | 433/172 |
| 5,733,124 A * | 3/1998 | Kwan | 433/172 |
| 5,947,735 A * | 9/1999 | Day | 433/173 |
| 6,050,819 A | 4/2000 | Robinson | 433/173 |
| 6,126,662 A | 10/2000 | Carmichael et al. | 433/173 |
| 6,217,331 B1 * | 4/2001 | Rogers et al. | 433/173 |

* cited by examiner

*Primary Examiner*—John J. Wilson
(74) *Attorney, Agent, or Firm*—Notaro & Michalos P.C.

(57) ABSTRACT

A universal dental implant arrangement includes both internal attachment and external attachment possibilities. This is achieved by utilizing an anchor having an internal void or abutment receiving bore, adapted for internal attachment-type abutments, along with a platform that can be used for various purposes. The universality of the implant is in providing the alternative of leaving the platform in place, causing the implant to function as an external attachment implant, or removing the platform and thereby converting the implant into an internal attachment implant. The platform can support an external attachment abutment or be remove so that the implant can accommodate an internal attachment abutment.

42 Claims, 9 Drawing Sheets

UNIVERSAL IMPLANT

FIELD AND BACKGROUND OF THE INVENTION

The present invention relates generally to the field of dentistry, and in particular, to a new and useful universal implant arrangement including a tapered and threaded anchor for implantation into the jaw bone of a mammal, means for rotating the anchor for seating it in the jaw bone, and means for mounting a replacement tooth or teeth to the anchor.

For the purpose of this disclosure and the claims forming a part thereof, relative terms and terms having functionally opposite but equivalent meanings such as, but not limited to, up, down, left, right, upwardly, downwardly, male and female, are used to include their opposite meaning. For, example, when referring to an implant anchor having a lower body portion with an upwardly facing opening, this is meant to also include an implant anchor having an upper body portion with a downwardly facing opening.

A wide variety of dental implant structures and systems is known.

U.S. Pat. No. 4,960,381 to Niznick, for example, discloses a screw-type dental implant anchor with an externally-threaded body portion joined to a top portion having an unthreaded exterior wall, and an internal, wrench-engaging surface.

U.S. Pat. No. 4,411,624 to Ogino, et al. discloses a dental implant with a dental root part having a substantial portion of the dental root surface to be placed in contact with the jaw bone, formed of a biologically active glass or glass-ceramic material that is contoured to have a selected taper.

U.S. Pat. No. 4,758,160 to Ismail discloses a dental implant having an alveolar surface and a hollow core therein, a prosthetic head having a shaft thereon, and a prosthesis. The shaft has a particular structure.

U.S. Pat. No. 4,863,383 to Grafelmann teaches a self-tapping screw implant.

U.S. Pat. No. 5,417,570 to Zuest, et al., U.S. Pat. No. 5,651,675 to Singer, U.S. Pat. No. 6,050,819 to Robinson and U.S. Pat. No. 6,126,662 to Carmichael et al., all disclose the use of the so called Morse taper in a dental implant.

U.S. Pat. No. 5,437,551 to Chalifoux teaches a dental system for insertion into a bore of a jaw bone of a patient which comprises an implant having a central bore extending from a top surface through a portion of the vertical height of the implant, one first extension extending from and directly attached to a first wall of the central bore, a dental post having a stem section shaped to fit into the central bore and having a second wall with at least one second extension attached directly to the post and positioned to frictionally fit with the first extension to retain the post within the central bore.

U.S. Pat. No. 5,199,873 discloses an implant with a stepped and threaded body for extending into the jaw bone.

Despite the effort of many practitioners in this field, a need remains for an effective universal dental implant arrangement.

SUMMARY OF THE INVENTION

It is an object of the present invention to provide a universal implant arrangement which includes an implant anchor, a platform or body that can be used, for example, for rotating the anchor to fix it in a jaw bone hole (and acts as an attachment surface for an external attachment abutment), and an abutment for mounting at least one tooth replacement, such as a crown or cap, to the anchor.

One of the main objects of the present invention is to provide a truly universal implant including both internal attachment and external attachment possibilities. This is achieved by utilizing an anchor having an internal void (also referred to here as a abutment receiving bore) adapted for internal attachment-type abutments, along with a (an attached) platform that can be used for various purposes. The universality of the implant is in providing the alternative of leaving the platform in place, causing the implant to function as an external attachment implant, or removing the platform and thereby converting the implant into an internal attachment implant. The platform can support an external attachment abutment or be remove so that the implant can accommodate an internal attachment abutment. For the purpose this disclosure the term "abutment" can mean any one or more of a wide variety of dental superstructures, such as a crown, a clip bar or spark erosion bar (that can be attached to more than one implant), a stud or post for helping support an over-denture, or the like. The external abutment can be attached to the platform, the platform thus providing any foundation needed for connecting the external abutment to the anchor.

Accordingly, another object of the invention is to provide a dental implant arrangement for attaching a replacement tooth to the jaw bone of a mammal, which has an anchor for implantation into the jaw bone. The anchor has a lower outer tapered surface and a thread in a preferred embodiment, although anchors without a thread and even without a tapered surface, may also be used. The anchor also has an upper portion with an upper surface and an abutment receiving bore extending into the anchor. A platform is attached to the upper surface of the anchor also for rotating the anchor in the jaw bone, when rotation is needed to install the anchor. A non-circular projection projects from and is part of the top of the platform. This can be used for engagement by a wrench for rotating the platform. Orientation structures such as co-rotation keys and/or a Morse taper, can also transmit rotation of the platform to the anchor. The orientation structures can also be used to orient an abutment to the correct rotational position with respect to the anchor. The abutment for supporting the tooth replacement may have a foundation extending into and fixed to the abutment receiving bore in the anchor when the tooth replacement is to be supported on the anchor as an internal attachment. Platform 24 may serve as a permanent part of the implant arrangement in that it forms the attachment location for the crown, or for hardware that supports the crown. The platform also serves as part of the installation process, for example, to rotate a threaded anchor into the jaw bone, and ultimately may be removed and replaced with an internal attachment abutment or other internal attachment structures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
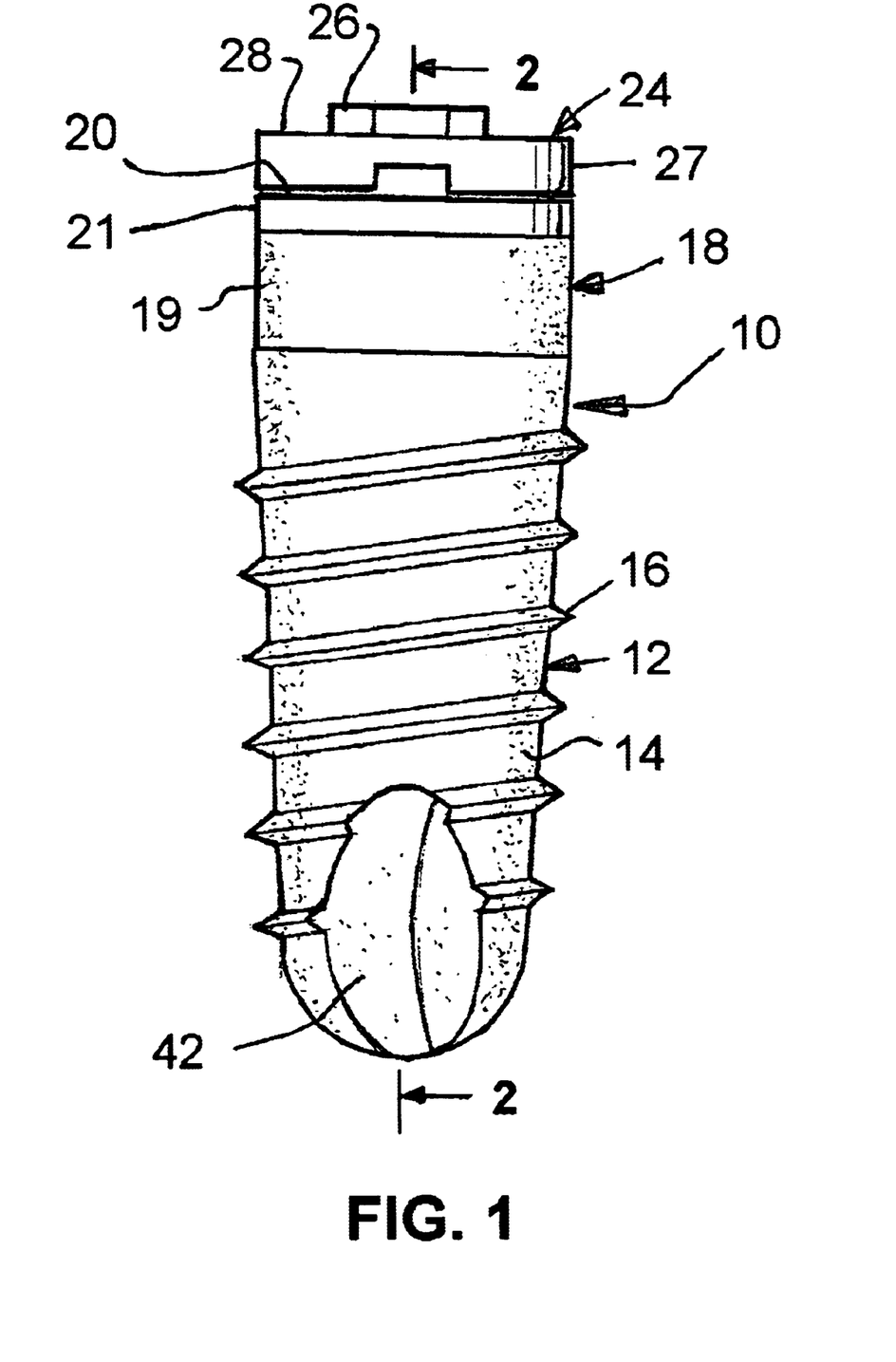
FIG. 1 is a side elevation of a first embodiment of the invention.

Referring now to the drawings, in which like reference numerals are used to refer to the same or similar elements, FIG. 1 illustrates a dental implant arrangement for attaching at least one replacement tooth to the jaw bone of a mammal.

The arrangement comprising an anchor 10 for implantation into a hole in the jaw bone, the anchor having a lower portion 12 with an outer tapered surface 14 and a thread 16 on the outer tapered surface. Thread 16 may or may not be present on surface 14. The anchor has an upper portion 18 with an upper or upwardly facing surface 20 and an abutment receiving bore 22 shown in FIG. 2, extending into the anchor and opening at the upper surface 20. Texturing or roughening of the surface 14 and/or thread 16 is accomplished, for example, by acid etching, plasma spray of titanium or blasting.

Figure 2:
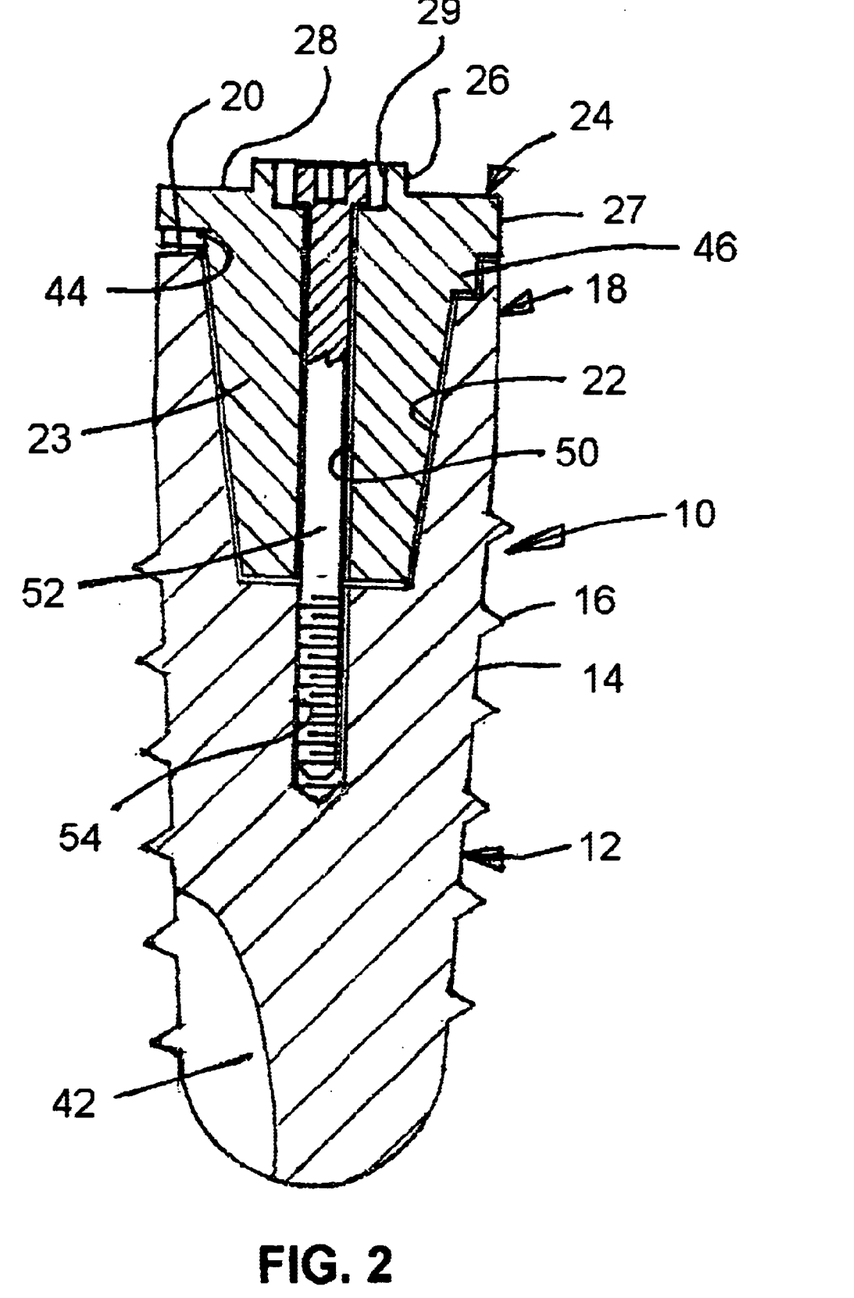
FIG. 2 is a sectional view taken along lines 2—2 of FIG. 1.
Figure 3:
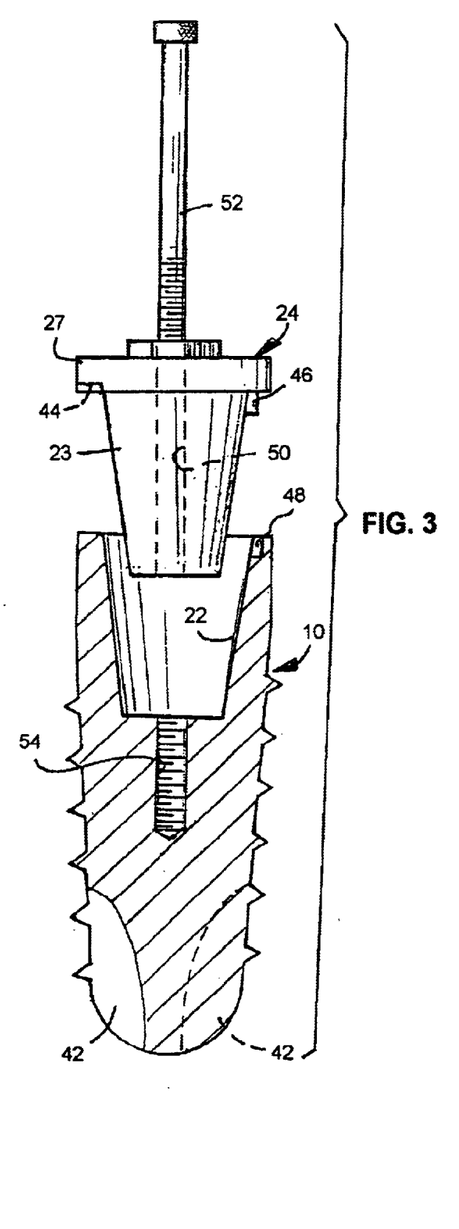
FIG. 3 is an exploded view of the embodiment of FIGS. 1 and 2.

A platform 24 is attached onto the upper surface 20 of the anchor 10 for rotating the anchor in the jaw bone hole. A non-circular projection 26 is fixed to and formed as one piece with a top surface 28 of the platform 24 and has at least one external wrench-engaging surface adapted for engagement by a wrench for rotating the platform and contiguous anchor thereby seating the anchor in the jaw bone. Projection 26, is made as one piece with the rest of the platform 24, e.g. of biocompatible metal. The wrench-engaging surface may be a hexagonal nut structure as shown, any other polygon or any other non-circular shape such as an oval so that a wrench can be used to turn the platform 24.

Orientation or co-rotation means are defined between the anchor 10 and the platform 24 for transmitting rotation of the platform to the anchor when the platform is still attached to the anchor as shown in FIGS. 1 and 2 and the platform is rotated using a wrench. It is noted that in embodiments that do not include the thread 16 on the anchor 10 (and therefore need not be rotated to install), the projection 26 may still be retained on the platform as a mechanism for receiving an abutment or other crown supporting structure on the platform. Such an abutment has a mating recess for the projection so as to fix a relative rotational position between the abutment and the anchor and prevent rotation of the dental superstructures. The orientation means also remains useful as a mechanism for the provided plural rotational positions between the abutment and the anchor.

Figures 5, 6:
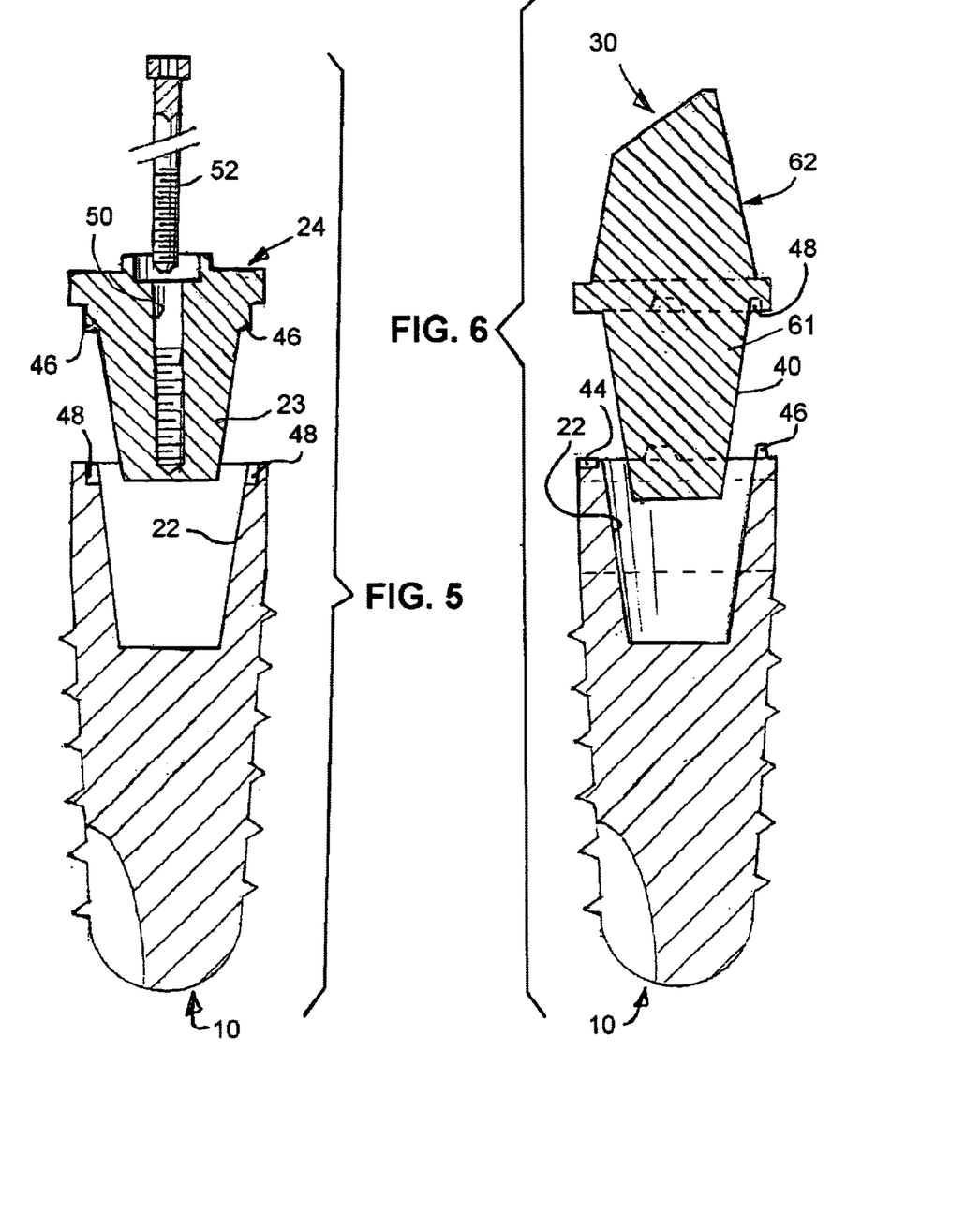
FIG. 5 is an exploded view of a still further embodiment of the invention.
FIG. 6 is an exploded view of another embodiment of the invention.
Figures 13, 14:
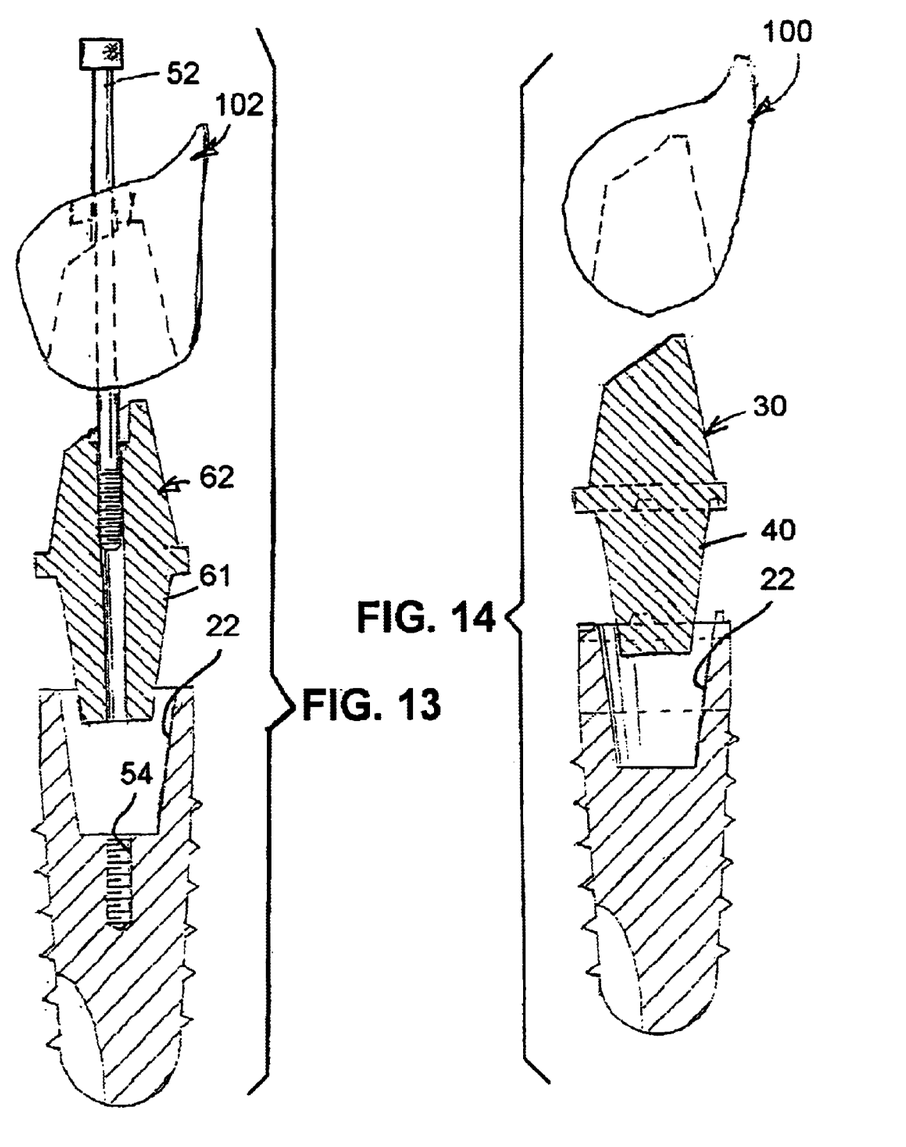
FIG. 13 is an exploded view of the embodiment of FIG. 8 showing a crown or cap used as a tooth replacement.
FIG. 14 is a view similar to FIG. 13 of the embodiment of FIG. 6 with a tooth replacement.

When used in its internal attachment implant application, platform 24 is removed and an abutment 30 shown in FIG. 6, adapted to support a tooth replacement such as a crown 100 in FIG. 14, is placed on the anchor. The abutment 30 includes a foundation 40 extending into and fixed to the abutment receiving bore 22 in the anchor 10, when the tooth replacement is to be supported on the anchor in its internal attachment application in a patient's mouth.

The outer tapered surface 14, e.g. in FIG. 1, and the thread 16, are textured to improve bone integration to the anchor. This is done in a know fashion, e.g. by coating the surfaces with a titanium plasma spray.

The upper portion 18 of the anchor 10 has a non-threaded and substantially cylindrical neck 19. The neck has an outer surface that is textured to improve bone integration to the anchor. A polished cylindrical collar 21 which is about 1 to 2 mm tall, is provided on the outer surface of the anchor, above the neck.

The platform has an upper, outer polished surface 27 that is contiguous with the cylindrical outer surfaces of the collar 21 and neck 19.

The anchor 10 includes one or more circumferentially spaced toe recesses 42 at a lower end of the anchor, for improving threading of the anchor to the bone of the jaw. Recess or recesses 42 cause the anchor to be self-threading in the bone as the anchor is rotated.

The implant anchor, in the embodiments of FIGS. 1–8 has a abutment receiving bore 22 in the form of a female Morse taper surface. Such surfaces having a taper or inclination of about 8° or less, have been found to securely fix a mating male Morse taper member due to the inter-frictional effects between the tapered surfaces.

The fixation is so secure that the co-rotation means can simply comprise the platform having a male Morse taper member 23 for frictionally engaging the female Morse taper surface of the abutment receiving bore 22.

The platform 24 also has a lower surface that closely engages and covers the upper surface 20 of the anchor 10.

Figure 4:
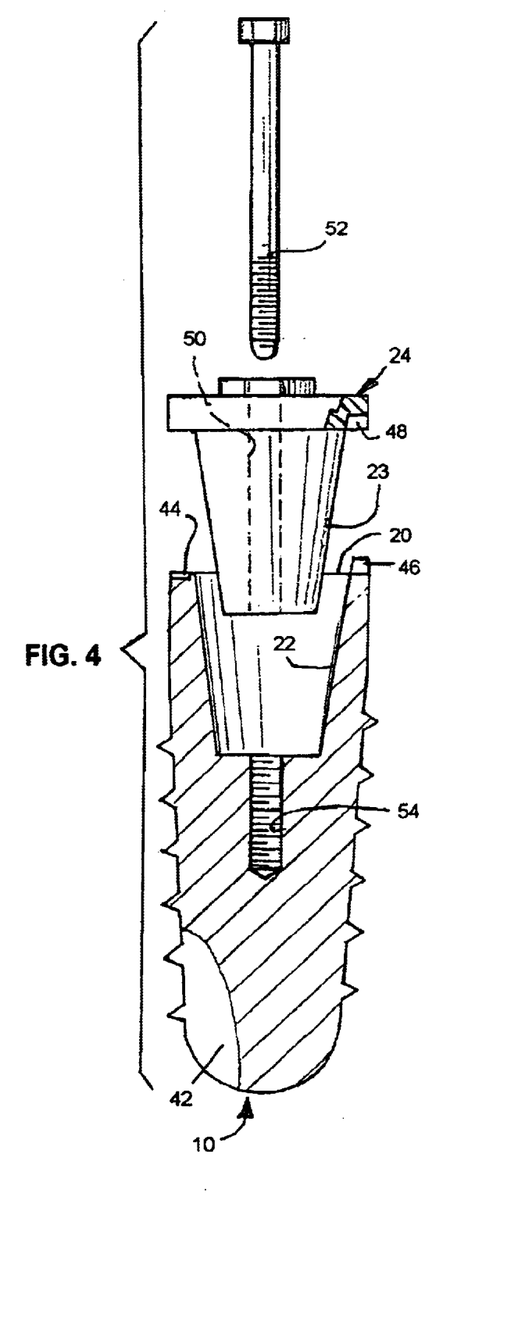
FIG. 4 is an exploded view of another embodiment that is similar to that of FIGS. 1 and 2.

A removal slot 44 either in the under surface of platform 24 as shown in FIG. 2, or on the upper surface 20 as shown in FIG. 4, but in any case between the lower surface of the platform and the upper surface of the anchor is provided for receiving a tool such as a small screw driver or like device, to overcome the frictional engagement of the Morse taper, and remove the platform 24 from the anchor 10.

A more positive co-rotation means comprises one or more circumferentially spaced male keys 46 (FIG. 4) projecting from either the platform or the anchor, and a corresponding female key recess 48 in the other for receiving the male key projection (FIG. 4). This also provided orientation means between the abutment and the anchor that permits an equal number of rotational position for the abutment on the anchor.

A screw bore 50 extends into the platform 24 and a fixing screw 52 extending into the screw bore, in the embodiments of FIGS. 2–5 and 7–9. The screw bore in the platform is at least partly threaded in the embodiment of FIG. 5, for holding an abutment such as abutment 60 in FIG. 7, to the platform 24. As shown is FIG. 7, the bore 50 in the platform can be partially or entirely threaded in order to receive threads of the screw 52 to fix the abutment 60. In this way, a shorter screw can be used which need not be threaded all the way into the anchor or the anchor may even be provided with no threaded bore. The same is true of FIG. 8 where part or all of the central bore through the abutment 62 may be threaded.

Figure 15:
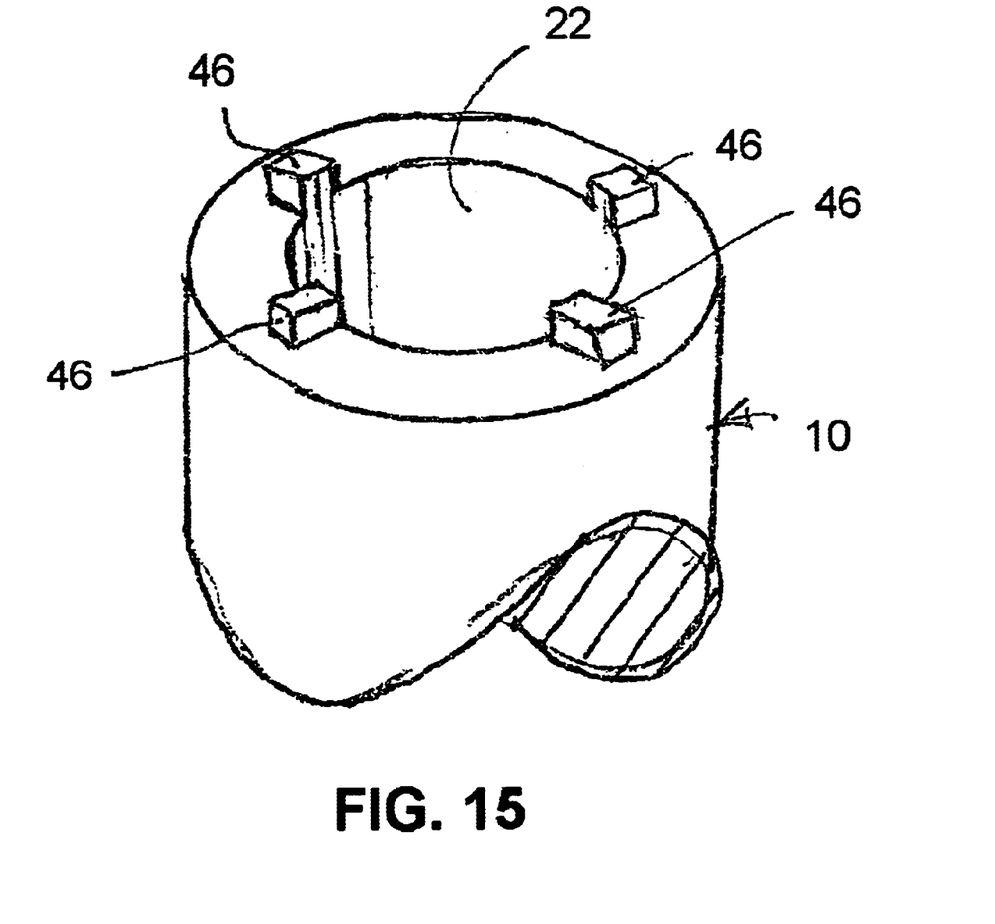
FIG. 15 is a view similar to FIG. 11 of another embodiment of the invention.

FIGS. 5 and 6 also illustrate how the use of multiple, e.g. six, sets of male and female keys 46,48, can be equally and circumferentially spaced around the implant (preferable with the female keys 48 in the top surface of the implant). In the case of off-axis abutments that are needed to accommodate implants that are at an angle to the axis of the crown to be installed (e.g. see FIGS. 6–8 of U.S. Pat. No. 5,417,570 to Zuest, et al.) this gives the practitioner an equal number of rotational positions to install the off-axis abutment. FIG. 15 shows four male keys 46 on the inner perimeter of the Morse taper surface 22 to provide the multiple position possibility for a platform and/or an abutment provided with four or more mating female key recesses. The inward placement of the keys also avoids the presence of an outer margin between the abutment and the anchor that is zig-zagged, since the keys are all spaced inwardly of the outer surface of the anchor. The line between these parts is a continuous circle which is thought to reduce the possibility of bacterial over growth.

In the embodiments of FIGS. 2–4 and 7–9, the screw bore has a threaded portion 54 that extends into the anchor 10, below the abutment receiving bore 22 for receiving the screw 52 for holding the platform to the anchor and/or for holding the abutment to the anchor, and/or for also holding a crown 102 to the abutment and anchor as in the embodiment of FIG. 13.

The non-circular wrench-engaging projection 26 contains a counter sink 29 (see FIG. 2, for example). This accommodates the head of the screw 52 in the counter sink. Screw 52 can be turned using a Allen wrench in an internal hex or other engagement recess in the screw head (FIG. 2), or a socket wrench on an external hex or other engagement surface (FIG. 4).

Figures 7, 8:
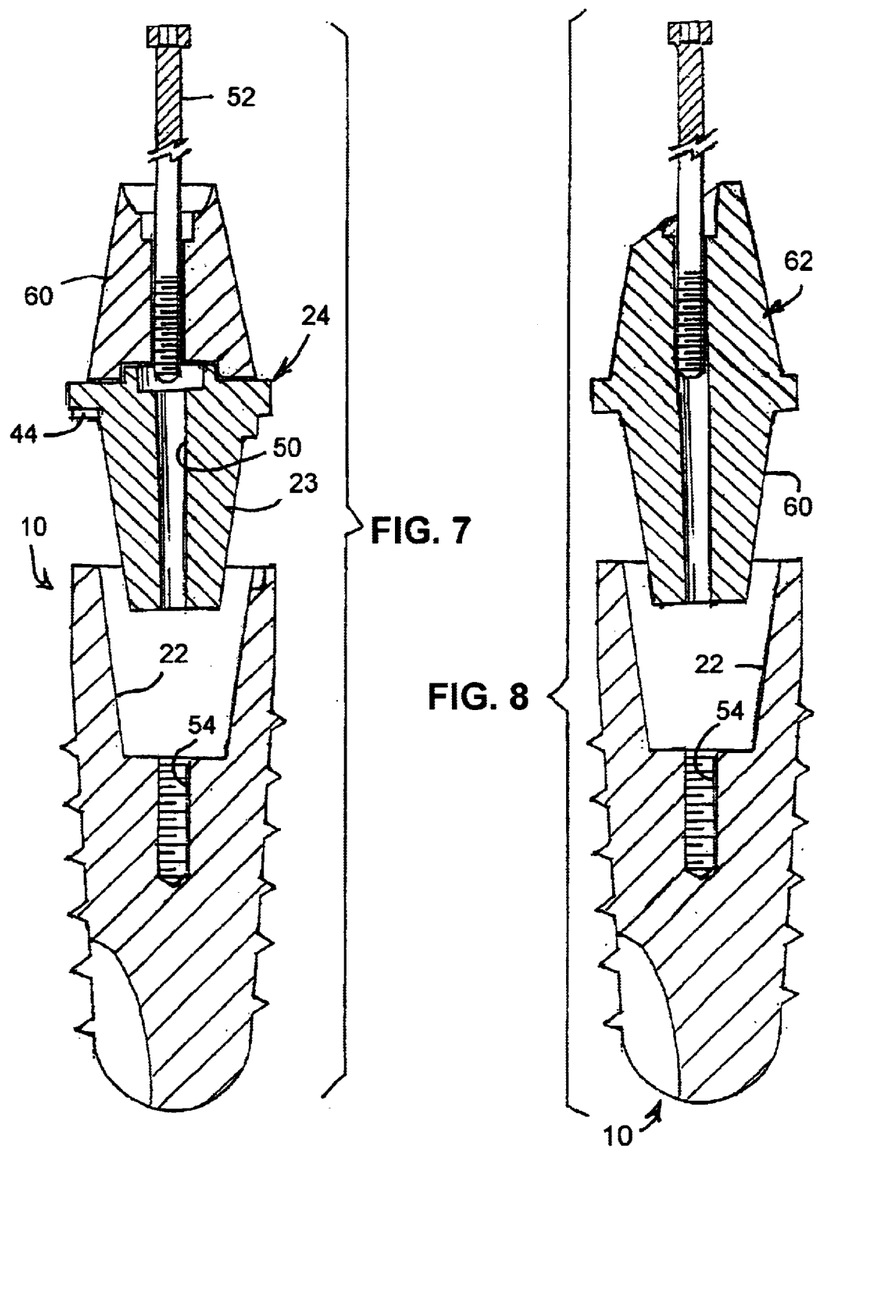
FIG. 7 is an exploded view of a still other embodiment of the invention.
FIG. 8 is an exploded view of another embodiment of the invention.

In its external application, the abutment 60 is attached to the male Morse taper member 23 of the platform in the embodiment of FIG. 7. In its internal attachment application, the abutment 62 with its foundation 61 having a male Morse taper member for frictionally engaging the female Morse taper surface of the abutment receiving bore, can be provided as shown in FIG. 8. FIG. 6 illustrates a similar internal attachment embodiment but without screw bore or screw.

Figure 9:
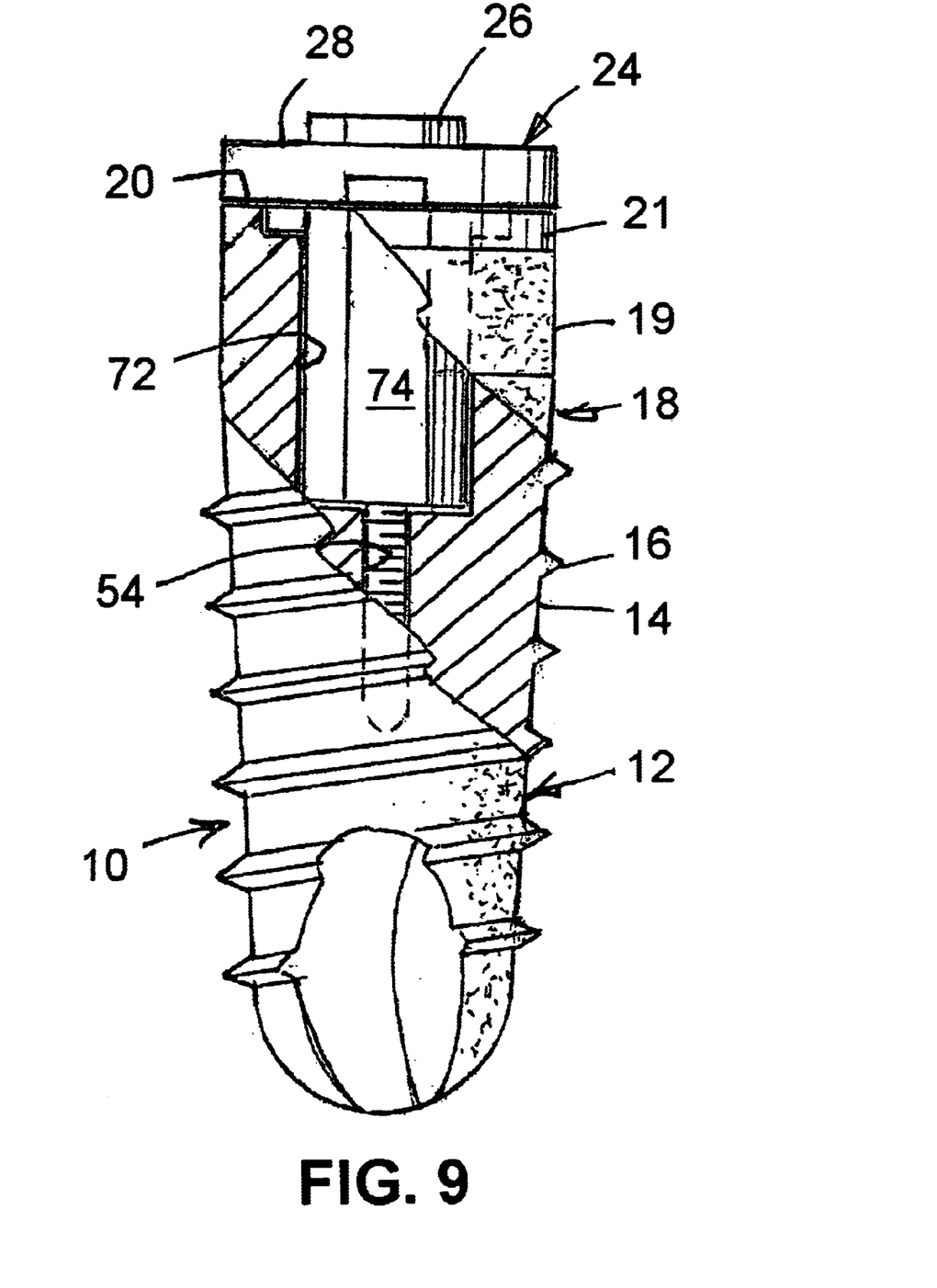
FIG. 9 is an elevation, partly in section of another embodiment.
Figure 10:
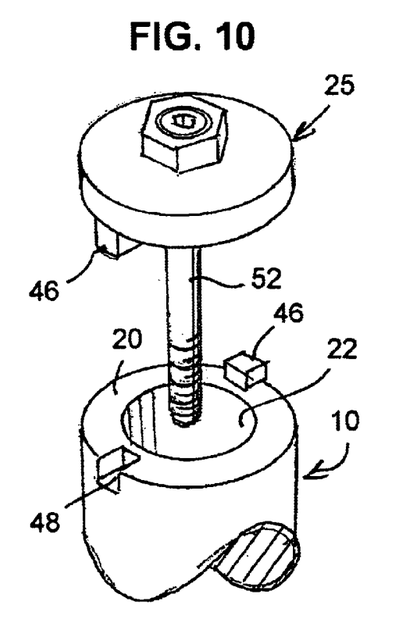
FIG. 10 is a partial perspective and exploded view of the platform and top of the anchor of another embodiment of the invention.
Figure 11:
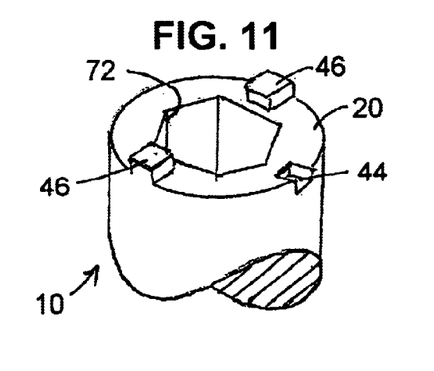
FIG. 11 is a partial perspective view of another embodiment.
Figure 12:
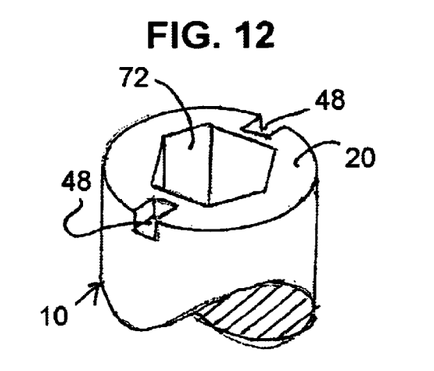
FIG. 12 is a view like FIG. 11 but of another embodiment of the invention.

As shown in FIGS. 9, 11 and 12, the abutment receiving bore 72 may be polygonal, e.g hexagonal. In these embodiments, the platform 24 includes a polygonal extension 74 extending from the platform, into the abutment receiving bore 72. In the embodiment of FIG. 10, a screw bore is provided through the platform 25, and the bore has a threaded portion 54 like that illustrated in FIG. 8, extending into the anchor 10, below the abutment receiving bore 22. The fixing screw 52 extends through the platform 25 and threads to the anchor 10 for holding the platform to the anchor. In this embodiment the platform is a cylindrical disk engaged onto the upper surface 20 of the anchor 10, with no portion extending into the abutment receiving bore 22. The same type of disk shaped platform 25 can be used with the polygonal bores of the anchors in FIGS. 11 and 12. In each male and mating female keys 46 and 48 act as the co-rotation or orientation means.

According to the invention a universal implant arrangement is provided in that the platform with external wrench-engaging projection can be used to seat the anchor, and if left in place acts as the top surface of the implant to which other dental superstructures can be externally attached. If, however, the platform is removed, other dental device superstructures may be internal attached to the anchor. An internal wrench-engaging device can be used either with the polygonal abutment receiving bore of FIG. 9, or even with a wrench outfitted with a Morse taper member. After this seating, a period of four to six months ensues during which time osseo-integration takes place on the external surface of the implant. After this period, the implant upon uncovering (stage two surgery) may be left as is and function as an external attachment implant. At that time it may also be converted to an internal attachment implant by removing the platform and using the internal bore as a receptacle for internal attachment structures.

After the period of integration, when the implant is uncovered (stage two surgery), a healing abutment is attached to the implant and soft tissue healing takes place. At this point the abutment of the invention is installed, either as the abutment 62 with its own foundation 61 (internal attachment application after platform 24 is removed), or the abutment 60 which uses the parts of the retained platform 24 extending into the abutment receiving bore 22 as the foundation (external attachment application).

The diameter at the top neck 19,21 of the anchor and contiguous platform surface 27, is about 2–8 mm and preferably 3–7 mm. The length of the implant from top surface 28 of the platform to the bottom of anchor 10 is about 5–18 mm and preferably 6–15 mm. The platform 24 is attached to the anchor 10 in the usual case when a product embodying the invention is supplied to a practitioner for use.

While specific embodiments of the invention have been shown and described in detail to illustrate the application of the principles of the invention, it will be understood that the invention may be embodied otherwise without departing from such principles.

What is claimed is:

1. A universal dental implant arrangement for attaching at least one replacement tooth to the jaw bone of a mammal and that is capable of being used in both internal and external attachment applications, the arrangement comprising:
   an anchor for implantation into a hole in the jaw bone, the anchor having a lower portion with an outer tapered surface including the thread, the anchor having an upper portion with an upper surface and an abutment receiving bore extending into the anchor and opening at the upper surface, the upper portion including a non-threaded cylindrical neck with an outer surface that is textured to improve bone integration to the anchor, and a cylindrical polished collar on an outer surface of the anchor, above the neck;
   a platform attached onto the upper surface of the anchor for rotating the anchor in the jaw bone hole and for attaching an abutment, the platform having an upper, outer polished surface that is contiguous with the cylindrical outer surfaces of the collar and neck;
   a non-circular projection fixed to a top surface of the platform, and having at least one external wrench-engaging surface adapted for engagement by a wrench for rotating the platform;
   orientation means defined between the anchor and the platform for establishing a plurality of relative rotational positions of the platform on the anchor when the platform is engaged to the anchor, the orientation means comprising co-rotation means defined between the anchor and the platform for transmitting rotation of the platform to the anchor when the platform is engaged to the anchor and is rotated; and
   an abutment adapted to support a tooth replacement, the abutment having a foundation extending into and fixed to the abutment receiving bore in the anchor when the tooth replacement is to be supported on the anchor.

2. An arrangement according to claim 1, including a toe recess at a lower end of the anchor for improving treading of the anchor to the bone of the jaw.

3. An arrangement according to claim 1, wherein the abutment receiving bore contains a female Morse taper surface.

4. An arrangement according to claim 3, wherein the orientation means includes the platform having a male Morse taper member for frictionally engaging the female Morse taper surface of the abutment receiving bore.

5. An arrangement according to claim 3, wherein the platform has a lower surface that closely engages and covered the upper surface of the anchor, and including a removal slot between the lower surface of the platform and the upper surface of the anchor for receiving a tool to remove the platform from the anchor.

6. An arrangement according to claim 1, wherein the orientation means comprises at least one male key projecting from one of the platform and the anchor, and a female key recess in the other of the platform and the anchor for receiving the male key projection.

7. An arrangement according to claim 1, including a screw bore extending into the platform and a fixing screw extending into the screw bore.

8. An arrangement according to claim 7, wherein the screw bore in the platform is at least partly threaded for holding the abutment to the platform.

9. An arrangement according to claim 7, wherein the screw bore has a threaded portion extended into the anchor below the abutment receiving bore for receiving the screw for holding the platform to the anchor.

10. An arrangement according to claim 1, wherein the non-circular projection is one of polygonal and oval.

11. An arrangement according to claim 10, wherein the non-circular projection contains a counter sink, and including a screw bore extending into the platform and a fixing screw extending into the screw bore and having a head contained in the counter sink.

12. An arrangement according to claim 1, wherein the abutment receiving bore contains a female Morse taper surface, the foundation of the abutment having a male Morse taper member for frictionally engaging the female Morse taper surface of the abutment receiving bore.

13. An arrangement according to claim 12, including a screw bore extending into the abutment and a fixing screw extending into the screw bore.

14. An arrangement according to claim 12, including a screw bore with a threaded portion extending into the anchor below the female Morse taper surface for receiving a screw to hold the abutment to the anchor.

15. An arrangement according to claim 1, wherein the foundation of the abutment comprises an extension of the platform that extends into the abutment receiving bore and screw means for holding the abutment to the platform.

16. An arrangement according to claim 1, wherein the abutment receiving bore is polygonal.

17. An arrangement according to claim 16, including a polygonal extension extending from the platform, into the abutment receiving bore.

18. An arrangement according to claim 16, including a screw bore through the platform and having a threaded portion extending into the anchor below the abutment receiving bore, a fixing screw extending through the platform and threaded to the anchor for holding the platform to the anchor, the platform being a cylindrical disk engaged onto the upper surface of the anchor with no portion extending into polygonal abutment receiving bore.

19. An arrangement according to claim 1, wherein the orientation means comprises at least one male key projecting from the platform, and a plurality of female key recesses equally circumferentially spaced around the anchor for receiving the male key, the abutment also having at least one male key projecting from it for engagement into one of the female key recesses to define a plurality of possible rotational positions between the abutment and the anchor.

20. A dental implant arrangement for attaching at least one replacement tooth to the jaw bone of a mammal, the arrangement comprising:
   an anchor for implantation into a hole in the jaw bone, the anchor having a lower portion with an outer tapered surface and a thread on the outer tapered surface, the anchor having an upper portion with an upper surface and an abutment receiving bore extending into the anchor and opening at the upper surface;
   a rotation body engaged onto the upper surface of the anchor for rotating the anchor in the jaw bone hole;
   a non-circular projection fixed to a top surface of the rotation body and having at least one external wrench-engaging surface adapted for engagement by a wrench for rotating the rotation body;

co-rotation means defined between the anchor and the rotation body for transmitting rotation of the rotation body to the anchor when the rotation body is engaged to the anchor and is rotated; and an abutment adapted to support a tooth replacement, the abutment having a foundation extending into and fixed to the abutment receiving bore in the anchor when the tooth replacement is to be supported on the anchor;

the upper portion of the anchor having a non-threaded neck with an outer surface that is textured to improve bone adhesion to the anchor, and a polished collar on an outer surface of the anchor, above the neck, the outer surfaces of the neck and collar being cylindrical, the rotation body having an upper, outer polished surface that is contiguous with the cylindrical outer surfaces of the collar and neck.

21. A dental implant arrangement according to claim 20, wherein the outer tapered surface and the thread are textures to improve bone adhesion to the anchor.

22. A dental implant arrangement according to claim 20, including a toe recess at a lower end of the anchor for improving treading of the anchor to the bone of the jaw.

23. A dental implant arrangement according to claim 20, wherein the abutment receiving bore contains a female Morse taper surface.

24. A dental implant arrangement according to claim 23, wherein the co-rotation means comprises the rotation body having a male Morse taper member for frictionally engaging the female Morse taper surface of the abutment receiving bore.

25. A dental implant arrangement according to claim 24, wherein the rotation body has a lower surface that closely engages and covered the upper surface of the anchor, and including a removal slot between the lower surface of the rotation body and the upper surface of the anchor for receiving a tool to remove the rotation body from the anchor.

26. A dental implant arrangement according to claim 23, wherein the screw bore has a threaded portion extending into the anchor below the female Morse taper surface for receiving the screw to hold the abutment to the anchor.

27. A dental implant arrangement according to claim 20, wherein the co-rotation means comprises at least one male key projecting from one of the rotation body and the anchor, and a female key recess in the other of the rotation body and the anchor for receiving the male key projection.

28. A dental implant arrangement according to claim 20, including a screw bore extending into the rotation body and a fixing screw extending into the screw bore.

29. A dental implant arrangement according to claim 28, wherein the screw bore in the rotation body is at least partly threaded for holding the abutment to the rotation body.

30. A dental implant arrangement according to claim 28, wherein the screw bore has a threaded portion extended into the anchor below the abutment receiving bore for receiving the screw for holding the rotation body to the anchor.

31. A dental implant arrangement according to claim 20, wherein the non-circular projection is one of polygonal and oval.

32. A dental implant arrangement according to claim 31, wherein the non-circular projection contains a counter sink, and including a screw bore extending into the rotation body and a fixing screw extending into the screw bore and having a head contained in the counter sink.

33. A dental implant arrangement according to claim 20, wherein the abutment receiving bore contains a female Morse taper surface, the foundation of the abutment having a male Morse taper member for frictionally engaging the female Morse taper surface of the abutment receiving bore.

34. A dental implant arrangement according to claim 33, including a screw bore extending into the abutment and a fixing screw extending into the screw bore.

35. A dental implant arrangement according to claim 20, wherein the foundation of the abutment comprises an extension of the rotation body that extends into the abutment receiving bore and screw means for holding the abutment to the rotation body.

36. A dental implant arrangement according to claim 20, wherein the abutment receiving bore is polygonal.

37. A dental implant arrangement according to claim 36, including a polygonal extension extending from the rotation body, into the abutment receiving bore.

38. A dental implant arrangement according to claim 37, including a screw bore through the rotation body and having a threaded portion extending into the anchor below the abutment receiving bore, a fixing screw extending through the rotation body and threaded to the anchor for holding the rotation body to the anchor, the rotation body being a cylindrical disk engaged onto the upper surface of the anchor with no portion extending into polygonal abutment receiving bore.

39. A dental implant arrangement according to claim 20, wherein the co-rotation means comprises at least one male key projecting from the rotation body, and a plurality of female key recesses equally circumferentially spaced around the anchor for receiving the male key, the abutment also having at least one male key projecting from it for engagement into one of the female key recesses to define a plurality of possible rotational positions between the abutment and the anchor.

40. A universal dental implant arrangement for attaching at least one replacement tooth to the jaw bone of a mammal and that is capable of being used in both internal and external attachment applications, the arrangement comprising:

an anchor for implantation into a hole in the jaw bone, the anchor having a lower portion with an outer surface, the anchor having an upper portion with an upper surface and an abutment receiving bore containing a female Morse taper surface and extending into the anchor and opening at the upper surface;

a platform attached onto the upper surface of the anchor;

a non-circular projection fixed to a top surface of the platform;

orientation means defined between the anchor and the platform for establishing a plurality of relative rotational positions of the platform on the anchor when the platform is engaged to the anchor; and an abutment adapted to support a tooth replacement, the abutment having a foundation extending into and fixed to the abutment receiving bore in the anchor when the tooth replacement is to be supported on the anchor;

the orientation means including the platform having a male Morse taper member for frictionally engaging the female Morse taper surface of the abutment receiving bore;

the platform having a lower surface that closely engages and covered the upper surface of the anchor, and including a removal slot between the lower surface of the platform and the upper surface of the anchor for receiving a tool to remove the platform from the anchor.

41. A dental implant arrangement for attaching at least one replacement tooth to the jaw bone of a mammal, the arrangement comprising:

an anchor for implantation into a hole in the jaw bone, the anchor having a lower portion with an outer tapered surface and a thread on the outer tapered surface, the anchor having an upper portion with an upper surface and an abutment receiving bore extending into the anchor and opening at the upper surface;

a rotation body engaged onto the upper surface of the anchor for rotating the anchor in the jaw bone hole;

a non-circular projection fixed to a top surface of the rotation body and having at least one external wrench-engaging surface adapted for engagement by a wrench for rotating the rotation body;

co-rotation means defined between the anchor and the rotation body for transmitting rotation of the rotation body to the anchor when the rotation body is engaged to the anchor and is rotated; and an abutment adapted to support a tooth replacement, the abutment having a foundation extending into and fixed to the abutment receiving bore in the anchor when the tooth replacement is to be supported on the anchor;

the abutment receiving bore contains a female Morse taper surface;

the co-rotation means comprises the rotation body having a male Morse taper member for frictionally engaging the female Morse taper surface of the abutment receiving bore.

42. A dental implant arrangement according to claim 41, wherein the rotation body has a lower surface that closely engages and covered the upper surface of the anchor, and including a removal slot between the lower surface of the rotation body and the upper surface of the anchor for receiving a tool to remove the rotation body from the anchor.

* * * * *